US011730682B2

(12) United States Patent
Shiroya et al.

(10) Patent No.: US 11,730,682 B2
(45) Date of Patent: Aug. 22, 2023

(54) SELF-STANDING COSMETIC SHEET

(71) Applicant: L'Oreal, Paris (FR)

(72) Inventors: Toshifumi Shiroya, Kanagawa (JP); Anne Laure Bernard, New York, NY (US); Christophe Dumousseaux, Shinjuku (JP)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/897,650

(22) Filed: Feb. 15, 2018

(65) Prior Publication Data

US 2018/0235849 A1 Aug. 23, 2018

Related U.S. Application Data

(62) Division of application No. 14/391,483, filed as application No. PCT/JP2012/060392 on Apr. 11, 2012, now Pat. No. 9,949,897.

(51) Int. Cl.
| | |
|---|---|
| *A61K 8/02* | (2006.01) |
| *A61K 8/67* | (2006.01) |
| *A61Q 15/00* | (2006.01) |
| *A61Q 17/00* | (2006.01) |
| *A61K 8/73* | (2006.01) |
| *A61Q 19/00* | (2006.01) |
| *A61K 8/81* | (2006.01) |
| *A61Q 19/02* | (2006.01) |
| *A61K 8/85* | (2006.01) |
| *A61Q 19/08* | (2006.01) |

(52) U.S. Cl.
CPC .............. *A61K 8/02* (2013.01); *A61K 8/0208* (2013.01); *A61K 8/676* (2013.01); *A61K 8/733* (2013.01); *A61K 8/736* (2013.01); *A61K 8/738* (2013.01); *A61K 8/8135* (2013.01); *A61K 8/85* (2013.01); *A61Q 15/00* (2013.01); *A61Q 17/00* (2013.01); *A61Q 19/00* (2013.01); *A61Q 19/02* (2013.01); *A61Q 19/08* (2013.01)

(58) Field of Classification Search
CPC .......... A61K 8/02; A61K 8/676; A61K 8/733; A61K 8/736; A61K 8/738; A61K 8/8135; A61K 8/85; A61K 8/0208; A61Q 15/00; A61Q 17/00; A61Q 19/00; A61Q 19/02; A61Q 19/08

See application file for complete search history.

(56) References Cited

U.S. PATENT DOCUMENTS

| | | | |
|---|---|---|---|
| 3,792,068 | A | 2/1974 | Luedders et al. |
| 4,717,720 | A | 1/1988 | Shroot et al. |
| 4,740,519 | A | 4/1988 | Shroot et al. |
| 4,925,658 | A | 5/1990 | Shroot et al. |
| 5,980,921 | A * | 11/1999 | Biedermann ............ A61K 8/42 424/401 |
| 6,423,854 | B1 | 7/2002 | Philippe et al. |
| 6,689,922 | B1 | 2/2004 | Bernardon |
| 2005/0244483 | A1 * | 11/2005 | Maruyama ........... A61K 8/0208 424/443 |
| 2006/0235370 | A1 * | 10/2006 | Oblong ................ A61B 18/203 606/9 |
| 2010/0062258 | A1 | 3/2010 | Takeoka et al. |
| 2010/0282269 | A1 | 11/2010 | Uchida et al. |
| 2011/0189287 | A1 | 8/2011 | Abbott et al. |
| 2012/0034466 | A1 | 2/2012 | Takeoka et al. |
| 2013/0142852 | A1 | 6/2013 | Tojo et al. |
| 2014/0120144 | A1 | 5/2014 | Abe et al. |

FOREIGN PATENT DOCUMENTS

| | | | |
|---|---|---|---|
| EP | 0199636 A1 | 10/1986 | |
| EP | 0227994 A1 | 7/1987 | |
| EP | 0325540 A1 | 7/1989 | |
| EP | 0402072 A2 | 12/1990 | |
| EP | 2082869 A1 * | 7/2009 | ................ C08J 5/18 |
| EP | 2082869 A1 | 7/2009 | |
| EP | 2589373 A1 | 5/2013 | |
| FR | 2180033 A1 | 11/1973 | |
| FR | 2570377 A1 | 3/1986 | |
| GB | 1404595 A | 9/1975 | |
| GB | 2197320 A | 5/1988 | |

(Continued)

OTHER PUBLICATIONS

Office Action for counterpart U.S. Appl. No. 14/391,483, dated Sep. 2, 2015.
Office Action for counterpart U.S. Appl. No. 14/391,483, dated Aug. 29, 2016.
Office Action for counterpart U.S. Appl. No. 14/391,483, dated Jul. 17, 2017.

(Continued)

*Primary Examiner* — Sean M Basquill
(74) *Attorney, Agent, or Firm* — The Marbury Law Group, PLLC

(57) ABSTRACT

The present invention relates to a cosmetic process which applies onto the skin a self-standing cosmetic sheet for the skin, comprising:

at least one biocompatible and/or biodegradable hydrophobic polymer layer wherein the self-standing cosmetic sheet has a thickness of from 10 to 1000 nm, preferably from 30 to 500 nm, and more preferably from 50 to 300 nm. The cosmetic sheet according to the present invention may comprise at least one cosmetic active ingredient.

The cosmetic sheet used in the present invention is very thin and not easily perceived on the skin; can be prepared with a variety of materials such as a biocompatible and/or biodegradable material; and can adhere well onto the skin without any adhesive layer so that it is less irritable or no irritable to the skin.

20 Claims, No Drawings

(56) References Cited

FOREIGN PATENT DOCUMENTS

| | | | | |
|---|---|---|---|---|
| JP | 2001-097842 A | 4/2001 | | |
| JP | 2005-527643 A | 9/2005 | | |
| JP | 2006-045169 A | 2/2006 | | |
| JP | 2006-517205 A | 2/2006 | | |
| JP | 2008069116 A | 3/2008 | | |
| JP | 2011136971 A | 7/2011 | | |
| JP | 2012-12317 A | 1/2012 | | |
| JP | 2012012337 A | 1/2012 | | |
| JP | 2013-071906 A | 4/2013 | | |
| JP | 2013-071907 A | 4/2013 | | |
| JP | 2013-184970 A | 9/2013 | | |
| JP | 5572263 B2 | 8/2014 | | |
| WO | 92/05764 A1 | 4/1992 | | |
| WO | 93/18743 A1 | 9/1993 | | |
| WO | 94/07844 A1 | 4/1994 | | |
| WO | 99/10318 A1 | 3/1999 | | |
| WO | 00/26167 A1 | 5/2000 | | |
| WO | 03/020231 A2 | 3/2003 | | |
| WO | WO-03020231 A2 * | 3/2003 | ........... | A61K 8/0208 |
| WO | 2006/025592 A1 | 3/2006 | | |
| WO | 2008/050913 A1 | 5/2008 | | |
| WO | 2008/140488 A2 | 11/2008 | | |
| WO | 2009/041121 A1 | 4/2009 | | |
| WO | 2012/002390 A1 | 1/2012 | | |

OTHER PUBLICATIONS

Final Office Action for counterpart U.S. Appl. No. 14/391,483, dated Feb. 6, 2017.
Final Office Action for counterpart U.S. Appl. No. 14/391,483, dated Mar. 16, 2016.
Japanese Office Action in related Application No. 2017-077394 dated Feb. 5, 2018.
Information Statement for counterpart JP Application No. 2014-549839 (Oct. 17, 2016) with translation.
Japanese Office Action for JP 2014-549839 (dated Jan. 8, 2016).
Takeoka, Shinji et al., "Development of biodegradable nanosheets as nanoadhesive plaster*," Pure Appl. Chem., vol. 80, No. 11, (2008), pp. 2259-2271.
Fujie, Toshinori et al, "Dual therapeutic action of antibiotic-loaded nanosheets for the treatment of gastrointestinal tissue defects," Biomaterials, Elsevier Science Publishers BV, Barking GB, vol. 31, No. 24, (Aug. 1, 2010), pp. 6269-6278.
International Search Report and Written Opinion for PCT/JP2012/060392, dated (Feb. 25, 2013).
Okamura, Yosuke et al., "Free-Standing Biodegradable Poly(lactic acid) Nanosheet for Sealing Operations in Surgery," Advanced Materials, 21, (2009), pp. 4388-4392.
Carl Thornfeldt, Chronic Inflammation is Etiology of Extrinsic Aging, 7 J. Cosmet. Dermatol., 78 (2008).
Fujie, Toshinori et al., "Ubiquitous Transference of a Free-Standing Polysaccharide Nanosheet with the Development of a Nano-Adhesive Plaster**," Advanced Materials, 19, (2007), pp. 3549-3553.
Fujie, Toshinori et al., "Sealing effect of a polysaccharide nanosheet for murine cecal puncture," Surgery, vol. 148, No. 1, (2010), pp. 48-58.
Catherine Huang, et al., The Truth About Over-the-Counter Topical Anti-Aging Products: A Comprehensive Review, 27 AESTH. Surg. J. 402 (2007).
English machine translation of JP 2011-136971 (Jul. 14, 2011).
English abstract of WO 2012/002390 (Jan. 5, 2012).
Japanese Office Action for counterpart Application No. 2017-077394, dated Feb. 25, 2020 (partial translation).
Ichimaru Pharcos Co., Ltd., "Skin Whitening," Fragrance Journal, 2004, vol. 32, No. 3, 7th page of the advertisement page after page 128 (the advertisement index page).
Efficacy, Effect and Action of New Cosmetic Material (1), CMC-group, Aug. 31, 1998, p. 376.
Fragrance Journal, 2001, vol. 29, No. 1, p. 95.

* cited by examiner

SELF-STANDING COSMETIC SHEET

CROSS REFERENCE TO RELATED APPLICATIONS

This application is a divisional of U.S. application Ser. No. 14/391,483, filed Oct. 9, 2014, the contents of which are incorporated herein by reference. This application claims the benefit of PCT/JP2012/060392, filed internationally on Apr. 11, 2012, which is incorporated herein by reference.

TECHNICAL FIELD

The present invention relates to a self-standing cosmetic sheet for the skin.

BACKGROUND ART

In order to apply makeup to the skin, there has been proposed a method of applying a cosmetic sheet in the form of a patch to the skin, in addition to a makeup method using cosmetic compositions.

For example, WO 2009/041121 has proposed a thin polyurethane-based sheet for cosmetic purposes, which is prepared by applying an adhesive to a polyurethane layer. This cosmetic sheet is used for, for example, reducing wrinkles on the skin by tensioning the skin with the sheet.

However, since the thickness of the thin polyurethane-based cosmetic sheet disclosed in WO 2009/0401121 is 2 to 20 microns, it is possible for the cosmetic sheet on the skin to be perceived.

One of the options to make the cosmetic sheet less perceived would be the reduction of the thickness of the sheet. However, a reduction of the thickness of such a cosmetic sheet affects the self-standing property, and therefore, the usability is deteriorated.

Furthermore, when a typical cosmetic sheet such as that disclosed in WO 2009/041121 includes an adhesive layer which is directly attached to the skin, the skin is sometimes irritated due to the adhesive layer. Also, it is possible for the adhesive layer to cause a rash on the skin as well.

One of the options to make the cosmetic sheet less of an irritant would be the removal of the adhesive layer. However, it is difficult for the cosmetic sheet to adhere onto the skin without an adhesive layer. JP-A-2011-136971 discloses a cosmetic sheet with no adhesive layer, but the materials for preparing the cosmetic sheet are very limited, and biodegradable polymers cannot be used.

Cosmetic sheets for the skin are required to have superior cosmetic effects such as good feel to touch of the skin, good skin pore or wrinkle hiding, and protection of the skin from pollution, contaminants and the like.

Furthermore, it is desirable for cosmetic sheets for the skin to provide extra cosmetic effects such as skin malodor reduction and whitening of the skin.

DISCLOSURE OF INVENTION

An objective of the present invention is to provide a cosmetic process using a self-standing cosmetic sheet which can provide superior cosmetic effects such as good feel to touch of the skin, change of skin appearance by, for example, good skin pore or wrinkle hiding, and protection of the skin from pollution, contaminants and the like.

The above objective of the present invention can be achieved by a cosmetic process for changing the appearance of skin, changing the feel to touch of the skin and/or protecting the skin, comprising the step of applying onto the skin a self-standing cosmetic sheet comprising at least one biocompatible and/or biodegradable hydrophobic polymer layer,
wherein
the self-standing cosmetic sheet has a thickness of from 10 to 1000 nm, preferably from 30 to 500 nm, and more preferably from 50 to 300 nm.

Another objective of the present invention is to provide a cosmetic process using a self-standing cosmetic sheet which can provide, in addition to the above properties, superior cosmetic effects such as treating the aging of the skin, absorbing sebum on the skin, controlling the perspiration on the skin, controlling odors on the skin, and delivering a cosmetic active ingredient via the skin.

The above objective of the present invention can be achieved by a cosmetic process for treating the aging of the skin, absorbing sebum on the skin, controlling the perspiration on the skin, controlling odors on the skin and/or delivering at least one cosmetic active ingredient via the skin, comprising the step of applying a self-standing cosmetic sheet comprising at least one biocompatible and/or biodegradable hydrophobic polymer layer,
wherein
the self-standing cosmetic sheet has a thickness of from 10 to 1000 nm, preferably from 30 to 500 nm, and more preferably from 50 to 300 nm, and
the cosmetic sheet comprises at least one cosmetic active ingredient, preferably selected from anti-sebum agents, anti-acne agents, deodorant agents, anti-perspirant agents, anti-bacterial agents, anti-aging agents, whitening agents or their mixtures.

The biocompatible and/or biodegradable hydrophobic polymer layer may be non-cross-linked, preferably selected from non-cross-linked poly(lactic acid) and derivatives thereof.

The biocompatible and/or biodegradable hydrophobic polymer layer may comprise at least one cationic polymer and at least one anionic polymer.

The cationic polymer may have at least one positively chargeable moiety selected from the group consisting of a quaternary ammonium group, a guanidine group, a biguanide group, an imidazole group, an imino group, a pyridyl group and an amino group.

The cationic polymer can be selected from the group consisting of chitosan, collagen, polyallylamines, polyvinylamines, polydiallyldialkyl ammonium chloride, polyanilines, polyvinylimidazoles, polydimethylaminoethylenemethacrylates, poly-1-methyl-2-vinylpyridine, polyamines, polyimines, polyethyleneimines, polyvinylpyridines, poly(quaternary pyridine), polylysines, polyomithines, polyarginines, polyhistidines, polyaminopropyl biguanides, and salts thereof.

The anionic polymer may have at least one negatively chargeable moiety selected from the group consisting of a sulfuric group, a sulfate group, a sulfonic group, a sulfonate group, a phosphoric group, a phosphate group, a phosphonic group, a phosphonate group, a carboxylic group and a carboxylate group.

The anionic polymer can be selected from the group consisting of alginic acid, hyaluronic acid, polyglutamic acids, polylactic acids, polyglycolic acids, polycaprolactones, poly(meth)acrylic acids, polyamic acids, polystyrene sulfonate, poly(vinyl sulfate), dextran sulfate, chondroitin sulfate, polymaleic acids, polyfumaric acids, carboxy methyl cellulose, styrene maleic anhydride derivatives and salts thereof.

The cosmetic active ingredient may be selected from anti-sebum agents, anti-acne agents, or the ingredients for the oily skin.

The cosmetic active ingredient may be a deodorant agent, an antiperspirant agent or an antibacterial agent. The deodorant agent may be selected from cyclodextrins and derivatives thereof.

The cosmetic active ingredient may be an anti-aging agent or a whitening agent.

The amount of the cosmetic active ingredient(s) can be from 0.01 to 30% by weight, preferably from 0.05 to 20% by weight, and more preferably from 0.1 to 10% by weight, relative to the total weight of the cosmetic sheet.

The self-standing cosmetic sheet used in the present invention may be attached to a substrate sheet. It is preferable that the cosmetic sheet be releasable from the substrate sheet.

Another objective of the present invention is to provide a self-standing cosmetic sheet for the skin which is very thin and not easily perceived, can be prepared with a variety of materials such as a biodegradable material, and can adhere well onto the skin without any adhesive layer, and can provide cosmetic effects such as treating the aging of the skin, absorbing sebum on the skin, controlling the perspiration on the skin, controlling odors on the skin and/or delivering at least one cosmetic active ingredient via the skin. In addition, the cosmetic effects may include anti-shine effects, skin malodor reduction effects and active ingredient delivery effects for whitening the skin. The self-standing cosmetic sheet can be used for the above cosmetic process.

The above objective of the present invention can be achieved by a self-standing cosmetic sheet for the skin as described above, wherein the cosmetic sheet comprises at least one cosmetic active ingredient.

BEST MODE FOR CARRYING OUT THE INVENTION

After diligent research, the inventors have discovered that it is possible to provide a cosmetic process which can provide superior cosmetic effects such as good feel to touch of the skin, change of skin appearance, and/or protection of the skin, by using a self-standing cosmetic sheet which is very thin, almost transparent, and not easily perceived on the skin; can be prepared with a variety of materials such as a biocompatible and/or biodegradable material; and can adhere well onto the skin without any adhesive layer so that it is less irritable or no irritable to the skin, and durable for long-term use. The cosmetic sheet can have good permeability to air and water, and good elasticity, due to the very thin thickness of the sheet.

The inventors also discovered that it is possible to provide a cosmetic process using a self-standing cosmetic sheet which can provide, in addition to the above properties, superior cosmetic effects such as treating the aging of the skin, absorbing sebum on the skin, controlling the perspiration on the skin, controlling odors on the skin, and/or delivering a cosmetic active ingredient via the skin.

Furthermore, the inventors also discovered that it is possible to provide a self-standing cosmetic sheet for the skin which can be used for the above cosmetic process according to the present invention.

Hereinafter, the cosmetic process according to the present invention and the self-standing cosmetic sheet used for the cosmetic process according to the present invention will be explained in more detail.

First Embodiment of Cosmetic Process

One embodiment of the present invention is a cosmetic process for changing the appearance of skin, changing the feel to touch of the skin, and/or protecting the skin, comprising the step of applying onto the skin, a self-standing cosmetic sheet for the skin, comprising:

at least one biocompatible and/or biodegradable hydrophobic polymer layer wherein the self-standing cosmetic sheet has a thickness of from 10 to 1000 nm, preferably from 30 to 500 nm, and more preferably from 50 to 300 nm.

Hereinafter, the cosmetic sheet used in the first embodiment of the present invention will be explained in more detail.

The cosmetic sheet used in the present invention is self-standing. The term "self-standing" in the specification means that the cosmetic sheet used in the present invention can be in the form of a sheet and can be handled as an independent sheet without the assistance of a substrate or support. Thus, the term "self-standing" may have the same meaning as "self-supporting".

The cosmetic sheet comprises at least one biocompatible and/or biodegradable polymer layer. Two or more biocompatible and/or biodegradable polymers may be used in combination. Thus, a single type of biocompatible and/or biodegradable polymer or a combination of different types of biocompatible and/or biodegradable polymers may be used.

The term "biocompatible" polymer in the specification means that the polymer does not have excess interaction between the polymer and cells in the living body including the skin, and the polymer is not recognized by the living body as a foreign material.

The term "biodegradable" polymer in the specification means that the polymer can be degraded or decomposed in a living body due to, for example, the metabolism of the living body itself or the metabolism of the microorganisms which may be present in the living body. Also, biodegradable polymer can be degraded by hydrolysis.

The term "hydrophobic" in the specification means that the solubility of the polymer in water (preferably with a volume of 1 liter) at from 20 to 40° C., preferably from 25 to 40° C., and more preferably from 30 to 40° C. is less than 10% by weight, preferably less than 5% by weight, more preferably less than 1% by weight, and even more preferably less than 0.1% by weight, relative to the total weight of the polymer. It is most preferable that the polymer is not soluble in water.

Since the cosmetic sheet used in the present invention uses a biocompatible and/or biodegradable polymer, it is less irritable or no irritable to the skin, and does not cause any rash. In addition, in combination with the very thin thickness and the use of a biocompatible and/or biodegradable polymer, the cosmetic sheet used in the present invention can adhere well to the skin.

As examples of the biocompatible and/or biodegradable polymer, mention may be made of polyvinylalcohol and derivatives thereof; polyethyleneoxides and derivatives thereof; polyvinylpyrrolidones and derivatives thereof; polylactic acid; polyamino acids; proteins such as caseins, albumins, and gelatins; polysaccharides such as glycogen, dextrin, dextran, hydroxypropylcellulose, agarose, chitin, and pullulan; and carboxyvinylpolymers.

The above polymer may or may not be cross-linked.

It is preferable to use, as the biocompatible and/or biodegradable polymer, a non-cross-linked polymer such as non-cross-linked polylactic acid and derivatives thereof. Two or more non-cross-linked polymers may be used in combination. Thus, a single type of non-cross-linked polymer or a combination of different types of non-cross-linked polymers may be used.

As the derivatives of polylactic acid, mention may be made of the polymer having the following repeating unit:

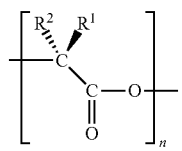

wherein $R^1$ and $R^2$ independently denote a hydrogen atom, an alkyl group, an aryl group or a halogen atom, provided that $R^1$ and $R^2$ do not simultaneously denote a hydrogen atom and a methyl group. The use of polylactic acid as a material for a self-standing thin sheet is disclosed in Adv. Mater., 21, 4388-4392, 2009, which is incorporated herein by reference.

It is also preferable to use, as the biocompatible and/or biodegradable polymer, a cross-linked polymer. Two or more cross-linked polymers may be used in combination. Thus, a single type of cross-linked polymer or a combination of different types of cross-linked polymers may be used. It may be preferable that the polymer be cross-linked in order to enhance the self-standing ability thereof. The use of as a material for a self-standing thin sheet is disclosed in Pure and Applied Chemistry, 80, 2259-2271, 2008, which is incorporated herein by reference.

It is possible to use a combination of at least one non-cross-linked polymer such as polylactic acid and at least one cross-linked polymer such as, as the biocompatible and/or biodegradable polymer.

The biocompatible and/or biodegradable polymer can preferably be prepared by comprises at least one cationic polymer and at least one anionic polymer. Thus, the biocompatible and/or biodegradable polymer can preferably comprise at least one cationic polymer and at least one anionic polymer. Two or more cationic or anionic polymers may be used in combination. Thus, a single type of cationic or anionic polymer or a combination of different types of cationic or anionic polymers may be used.

The cationic polymer may have at least one positively chargeable moiety selected from the group consisting of a quaternary ammonium group, a guanidine group, a biguanide group, an imidazole group, an imino group, a pyridyl group and an amino group.

The cationic polymer can be selected from the group consisting of chitosan, collagen, polyallylamines, polyvinylamines, polydiallyldialkyl ammonium chloride, polyanilines, polyvinylimidazoles, polydimethylaminoethylenemethacrylates, poly-1-methyl-2-vinylpyridine, polyamines, polyimines, polyethyleneimines, polyvinylpyridines, poly(quaternary pyridine), polylysines, polyomithines, polyarginines, polyhistidines, polyaminopropyl biguanides, and salts thereof. Chitosan is preferable.

The anionic polymer may have at least one negatively chargeable moiety selected from the group consisting of a sulfuric group, a sulfate group, a sulfonic group, a sulfonate group, a phosphoric group, a phosphate group, a phosphonic group, a phosphonate group, a carboxylic group and a carboxylate group.

The anionic polymer can be selected from the group consisting of alginic acid, hyaluronic acid, polyglutamic acids, polylactic acids, polyglycolic acids, polycaprolactones, poly(meth)acrylic acids, polyamic acids, polystyrene sulfonate, poly(vinyl sulfate), dextran sulfate, chondroitin sulfate, polymaleic acids, polyfumaric acids, carboxy methyl cellulose, styrene maleic anhydride derivatives and salts thereof. Alginic acid or salt thereof is preferable, and sodium alginate is more preferable.

The self-standing cosmetic sheet according to the present invention has a thickness of from 10 to 1000 nm, preferably from 30 to 500 nm, more preferably from 50 to 300 nm, even more preferably from 70 to 200 nm, and most preferably from 80 to 150 nm.

It is possible to prepare such a self-standing cosmetic sheet with a very thin thickness by, for example, alternately laminating a cationic polymer and an anionic polymer or vise versa. Due to the alternate lamination, the positive charge of the cationic polymer and the anionic charge of the anionic polymer are electrostatically attracted to each other, and form a cross-linked structure which can be advantageous to enhance the self-standing property of the cosmetic sheet.

The alternate lamination can be performed by, for example, spin-coating of a support such as a $SiO_2$ support using a cationic polymer solution and an anionic polymer solution alternately. The preparation of a very thin sheet by the spin-coating of a $SiO_2$ support with a solution of a cationic polymer such as chitosan and a solution of an anionic polymer such as sodium alginate is disclosed in Adv. Mater., 19, 3549-3553, 2007 and Surgery, 148, 48-58, 2010, which are incorporated herein by reference.

It is preferable for the cosmetic sheet according to the present invention to comprises a biocompatible and/or biodegradable polymer layer comprising at least one cationic polymer and at least one anionic polymer, because the polymer prepared by the cationic and anionic polymers can be hydrophobic, and therefore, the cosmetic sheet according to the present invention can be water-resistance, and can have enhanced durability.

The cosmetic sheet can be applied onto the skin for cosmetic purposes, such as for deodorization, skin care or make-up.

It is preferable for the cosmetic sheet according to the present invention to comprises a biocompatible and/or biodegradable polymer layer comprising at least one cationic polymer and at least one anionic polymer, because it can catch acidic and basic malodor molecules by the cationic and anionic groups, respectively, in the polymer, and/or it can have antibacterial properties (cationic polymers such as polylysines have antibacterial properties).

The first embodiment of the present invention is a cosmetic process for changing the appearance of skin, changing the feel to the touch of the skin, and/or protecting the skin.

The above cosmetic process can be performed by using the self-standing cosmetic sheet as described above even if the cosmetic sheet does not comprise any cosmetic active ingredient.

For example, the self-standing cosmetic sheet can immediately change or modify the appearance of the skin by changing light reflection on the skin and the like. Therefore, it is possible for the self-standing cosmetic sheet to conceal skin defects such as pores or wrinkles. Further, the self-standing cosmetic sheet can immediately change or modify the feel to the touch of the skin by changing the surface roughness on the skin and the like. Furthermore, the self-standing cosmetic sheet can immediately protect the skin by covering the surface of the skin and shield the skin, as a barrier, from environmental stresses such as pollution, contaminants and the like.

Thus, the term "cosmetic process for protecting the skin" means that the self-standing cosmetic sheet can protect the skin by covering the surface of the skin and shield the skin, as a barrier, from environmental stresses such as pollution, contaminants and the like.

The above cosmetic effects can be adjusted or controlled by changing the chemical composition, the thickness and/or the surface roughness of the cosmetic sheet.

It is also possible to apply a makeup cosmetic composition onto the cosmetic sheet after being applied onto the skin.

It is preferable that the self-standing cosmetic sheet be used under the conditions whereby it is attached to a substrate sheet, because the application of the cosmetic sheet to the skin becomes easier. For example, the composite sheet of the cosmetic sheet and the substrate sheet can be applied onto the skin such that the cosmetic sheet directly touches the skin, and the substrate sheet can be removed by peeling off from the cosmetic sheet or washed with water if the cosmetic sheet is hydrophobic and the substrate sheet is water-soluble. Thus, the cosmetic sheet alone can be left on the skin.

Second Embodiment of Cosmetic Process and Self-Standing Cosmetic Sheet

The second embodiment of the present invention is a cosmetic process for treating the aging of the skin, absorbing sebum on the skin, controlling the perspiration on the skin, controlling odors on the skin, and/or delivering at least one cosmetic active ingredient via the skin, comprising the step of applying onto the skin a self-standing cosmetic sheet for the skin, comprising:
at least one biocompatible and/or biodegradable hydrophobic polymer layer
wherein
the self-standing cosmetic sheet has a thickness of from 10 to 1000 nm, preferably from 30 to 500 nm, and more preferably from 50 to 300 nm; and
the cosmetic sheet comprises at least one cosmetic active ingredient, preferably selected from anti-sebum agents, anti-acne agents, deodorant agents, anti-perspirant agents, antibacterial agents, anti-aging agents, whitening agents or their mixtures.

Another aspect of the present invention is a self-standing cosmetic sheet itself as described above. The self-standing cosmetic sheet according to the present invention is intended to be applied onto the skin.

Hereinafter, the cosmetic sheet according to the present invention which is used in this second embodiment of the present invention will be explained in a more detailed manner.

The cosmetic sheet used in the second embodiment of the present invention includes at least one cosmetic active ingredient in the cosmetic sheet, preferably in the biocompatible and/or biodegradable hydrophobic polymer layer, used in the cosmetic process according to the first embodiment of the present invention.

There is no limit to the cosmetic active ingredient. Two or more cosmetic active ingredients may be used in combination. Thus, a single type of cosmetic active ingredient or a combination of different types of cosmetic active ingredients may be used.

According to the present invention, the cosmetic active ingredient may be an anti-sebum agent. The cosmetic sheet according to the present invention including an anti-sebum agent can change the appearance of the skin by reducing the shiny appearance due to the sebum. In addition, since the anti-sebum agent is in the sheet, the skin is protected from detrimental external factors. Thus, the cosmetic sheet according to the present invention including an anti-sebum agent can be less irritable or no irritable to the skin.

As examples of the anti-sebum agent, mention may be made of zinc salts such as zinc lactate, zinc gluconate, zinc pidolate, zinc carboxylate, zinc salicylate and zinc cysteate; and magnesium salts such as magnesium carbonate, magnesium silicate, magnesium nitrate, magnesium sulfate, magnesium acetate, magnesium citrate and magnesium oxide.

It is also possible for the cosmetic active ingredient to be selected from seboregulatory agents such as retinoids, and particularly retinol; sulphur and sulphur-containing derivatives; selenium chloride; vitamin B6 or pyridoxine; the mixture of capryloylglycine, sarcosine and extract of *Cinnamomum zeylanicum* sold in particular by Seppic under the trade name Sepicontrol A5®; an extract of *Laminaria saccharina* sold in particular by Secma under the trade name Phlorogine®; an extract of *Spiraea ulmaria* sold in particular by Silab under the trade name Sebonormine®; plant extracts of the species *Arnica montana, Cinchona succirubra, Eugenia caryophyllata, Humulus lupulus, Hypericum perforatum, Mentha piperita, Rosmarinus officinalis, Salvia officinalis* and *Thymus vulgaris*, all sold, for example, by Maruzen; an extract of *Serenoa repens*, sold in particular by Euromed; plant extracts of the genus *Silybum*; plant extracts containing sapogenins, and especially the diosgenin-rich extracts of Dioscoreaceae; and extracts of *Eugenia caryophyllata* containing eugenol and eugenyl glucoside.

According to the present invention, the cosmetic active ingredient may be an anti-acne agent.

According to the present invention, the cosmetic active ingredient may be a deodorant agent, an antiperspirant agent or an antibacterial agent.

As examples of the deodorant agent, mention may be made of chelating agents such as EDTA and DPTA; inhibitors for enzymes involving the formation of malodor compounds, such as inhibitors for arylsulfatase, 5-lipoxygenase, aminoacylase, and beta-glucuronidase; zeolites; cyclodextrins; and metal oxide silicates.

It is preferable that the deodorant agent be selected from cyclodextrins and derivatives thereof. Any type of cyclodextrins and derivatives thereof can be used. The cyclodextrin that can be used can be selected from, for example, oligosaccharides of formula:

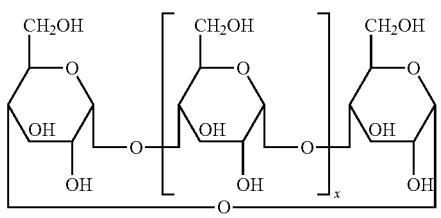

wherein x is selected from 4 (corresponding to α-cyclodextrin), 5 (corresponding to β-cyclodextrin) and 6 (corresponding to γ-cyclodextrin). In one embodiment, the cyclodextrin can be selected from β-cyclodextrin and γ-cyclodextrin, for example, β-cyclodextrin. A β-cyclodextrin sold by the company WACKER under the name CAVAMAX W7 PHARMA and a γ-cyclodextrin sold by the company WACKER under the name CAVAMAX W8 can, for example, be used. In another embodiment, the derivatives of cyclodextrin can be selected from, for example, methylcyclodextrins such as the methyl-β-cyclodextrin sold by the company WACKER under the name CAVASOL W7.

As examples of the antiperspirant agent, mention may be made of aluminum salts, zirconium salts and zinc salts as mentioned above. Antiperspirant aluminum salts are preferable. As used herein, the term "antiperspirant aluminum salt" means any salt or any aluminum complex that has the effect of reducing or limiting the flow of sweat. The aluminum salt in accordance with the present disclosure may be, for example, selected from aluminum halohydrates; aluminum zirconium halohydrates; and complexes of zirconium hydroxychloride and of aluminum hydroxychloride with an amino acid, such as those described in U.S. Pat. No. 3,792,068, which are commonly known as "ZAG complexes". Among the aluminum salts that may be mentioned, for example, are aluminum chlorohydrate in activated or unactivated form, aluminum chlorohydrex, aluminum chlorohydrex polyethylene glycol complex, aluminum chlorohydrex propylene glycol complex, aluminum dichlorohydrate, aluminum dichlorohydrex polyethylene glycol complex, aluminum dichlorohydrex propylene glycol complex, aluminum sesquichloro-hydrate, aluminum sesquichlorohydrex polyethylene glycol complex, aluminum sesquichlorohydrex propylene glycol complex, and aluminum sulfate buffered with sodium aluminum lactate. Among the aluminum zirconium double salts that may be mentioned, for example, are aluminum zirconium octachlorohydrate, aluminum zirconium pentachloro-hydrate, aluminum zirconium tetrachlorohydrate, and aluminum zirconium trichlorohydrate. An example of an aluminum zirconium double salt is the product sold by the company Reheis under the name Reach AZP-908-SUF. The complexes of zirconium hydroxychloride and of aluminum hydroxychloride with an amino acid are generally known under the name ZAG (when the amino acid is glycine). Among these products, mention may be made of the aluminum zirconium octachlorohydrex glycine, aluminum zirconium pentachlorohydrex glycine, aluminum zirconium tetrachlorohydrex glycine, and aluminum zirconium trichlorohydrex glycine complexes.

As examples of the antibacterial agent, mention may be made of 2,4,4'-trichloro-2'-hydroxydiphenyl ether (or triclosan), 3,4,4'-trichlorocarbanilide, phenoxyethanol, phenoxypropanol, phenoxyisopropanol, hexamidine isethionate, metronidazole and its salts, miconazole and its salts, itraconazole, terconazole, econazole, ketoconazole, saperconazole, fluconazole, clotrimazole, butoconazole, oxiconazole, sulfaconazole, sulconazole, terbinafine, ciclopiroxe, ciclopiroxol-amine, undecylenic acid and its salts, benzoyl peroxide, 3-hydroxybenzoic acid, 4-hydroxybenzoic acid, phytic acid, N-acetyl-L-cysteine acid, lipoic acid, azelaic acid and its salts, arachidonic acid, resorcinol, octopirox, octoxyglycerol, octanolglycine, caprylyl glycol, 10-hydroxy-2-decanoic acid, dichlorophenyl imidazole dioxolane and its derivatives described in Patent WO9318743, copper pidolate, salicylic acid, iodopropynyl butylcarbamate, farnesol, phytosphingosines and mixtures thereof. In addition, metal salts which can provide metal ions such as silver ions may be used.

According to the present invention, the cosmetic active ingredient may be an anti-aging agent or a whitening agent.

The anti-aging active agent may be any active agent capable of treating or preventing any sign of ageing of the skin.

As examples of the anti-aging agent, mention may be made of moisturizers, free-radical scavengers, keratolytic agents, vitamins, anti-elastase and anti-collagenase agents, protides, fatty acid derivatives, steroids, trace elements, bleaching agents, extracts of algae and of planktons, sunscreens, enzymes and coenzymes, flavonoids and ceramides, and mixtures thereof.

I. Useful moisturizers include sodium lactate; polyols, and in particular glycerol, sorbitol and polyethylene glycols; mannitol; amino acids; hyaluronic acid; lanolin; urea and mixtures containing urea, such as NMF ("Natural Moisturizing Factor"); petroleum jelly; and mixtures thereof.

II. Useful free-radical scavengers include phosphonic acid derivatives such as ethylenediaminetetra(methylenephosphonic acid), hexamethylenediaminetetra(methylenephosphonic acid), diethylenetriaminepenta(methylenephosphonic acid), and their salts and in particular their sodium salts, such as pentasodium ethylenediaminetetra(methylenephosphonic acid); ethylenediaminetetraacetic acid and its salts such as sodium salt; guanosine; superoxydismutase; tocopherol (vitamin E) and its derivatives (acetate); ethoxyquine; lactoferrin; lactoperoxidase and nitroxide derivatives; superoxide dismutases; glutathione peroxidase; plant extracts with free-radical-scavenging activity, such as the aqueous extract of wheatgerm sold by the company Silab under the reference Detoxiline; and mixtures thereof.

III. Useful keratolytic agents include α-hydroxy acids, especially acids derived from fruit, for instance glycolic acid, lactic acid, malic acid, citric acid, tartaric acid and mandelic acid, derivatives thereof and mixtures thereof; β-hydroxy acids, for instance salicylic acid and its derivatives such as 5-n-octanoylsalicylic acid or 5-n-dodecanoylsalicylic acid; α-keto acids, for instance ascorbic acid or vitamin C and its derivatives such as its salts, for instance sodium ascorbate, magnesium ascorbyl phosphate or sodium ascorbyl phosphate; its esters, for instance ascorbyl acetate, ascorbyl palmitate and ascorbyl propionate, or its sugars, for instance glycosylated ascorbic acid, and mixtures thereof; β-keto acids; retinoids, for instance retinol (vitamin A) and its esters, retinal, retinoic acid and its derivatives, and also the retinoids described in documents FR-A-2,570,377, EP-A-199 636, EP-A-325-540 and EP-A-402 072; and mixtures thereof.

IV. Useful vitamins, in addition to vitamins A, E and C indicated above, include vitamin B3 (or vitamin PP or niacinamide), vitamin B5 (or panthenol), vitamin D, vitamin F, derivatives, analogues and precursors of these vitamins and also those of vitamins A, E and C, for instance lycopenes or carotenes that are precursors of vitamin A, and mixtures thereof.

Vitamin B3, also known as vitamin PP, is a compound of formula:

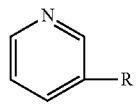

in which R may be —CONH$_2$ (niacinamide), —COOH (nicotinic acid or niacin), —CH$_2$OH (nicotinyl alcohol), —CO—NH—CH$_2$—COON (nicotinuric acid) or —CO—NH—OH (nicotinyl hydroxamic acid). Vitamin B3 derivatives include nicotinic acid esters, such as tocopherol nicotinate; amides derived from niacinamide by substitution of the hydrogen groups of —CONH$_2$; products of reaction with carboxylic acids and amino acids; esters of nicotinyl alcohol and of carboxylic acids such as acetic acid, salicylic acid, glycolic acid or palmitic acid. Mention may also be made of the following derivatives:

2-chloronicotinamide, 6-methylnicotinamide, 6-aminonicotinamide, N-methylnicotinamide, N,N-dimethylnicotinamide, N-(hydroxymethyl)nicotinamide, quninolinic acid imide, nicotinanilide, N-benzylnicotinamide, N-ethylnicotinamide, nifenazone, nicotinaldehyde, isonicotinic acid, methylisonicotinic acid, thionicotinamide, nialamide, 2-mercaptonicotinic acid, nicomol and niaprazine. Other vitamin B3 derivatives which may also be mentioned include its mineral salts such as the chlorides, bromides, iodides and carbonates, and its organic salts, such as the salts obtained by reaction with carboxylic acids such as acetate, salicylate, glycolate, lactate, malate, citrate, mandelate, tartrate, etc.

As vitamin B5, it is also possible to use panthenol or panthenyl alcohol or 2,4-dihydroxy-N(3-hydroxypropyl)-3,3-dimethylbutanamide, in its various forms: D-panthenol, DL-panthenol, and its derivatives and analogues, such as calcium pantothenate, pantethine, pantotheine, ethyl panthenyl ether, pangamic acid, pyridoxine and pantoyllactose, and natural compounds containing them such as royal jelly.

As vitamin D, mention may be made of 1α,25-dihydroxy vitamin D3 and its analogues, and also vitamin D analogues, such as those described in document WO-A-00/26167, such as, for example:

3-hydroxymethyl-5-{2-[3-(5-hydroxy-5- or 6-methyl-hexyl)-phenyl]-vinyl}-phenol,
3-[3-(5-hydroxy-1,5-dimethyl-hexyl)-phenoxymethyl]-5-hydroxymethyl-phenol,
6-[3-(3,4-bis-hydroxymethyl-benzyloxy)-phenyl]-2-methyl-hepta-3,5-dien-2-ol,
6-[3-(3,4-bis-hydroxymethyl-benzyloxy)-phenyl]-2-methyl-hexan-2-ol,
6-[3-(3,4-bis-hydroxymethyl-phenoxymethyl)-phenyl]-2-methyl-heptan-2-ol,
7-[3-(3,4-bis-hydroxymethyl-phenoxymethyl)-phenyl]-3-ethyl-octan-3-ol,
5-{2-[4-(5-hydroxy-5-methyl-hexyl)-phenyl]-vinyl or -ethyl}-benzene-1,3-diol,
5-{2-[3- or 4-(6-hydroxy-6-methyl-heptyl)phenyl]vinyl}-benzene-1,3-diol,
5-{2-[3- or 4-(6-hydroxy-6-methyl-heptyl)-phenyl]ethyl-benzene-1,3-diol,
2-hydroxymethyl-4-{2-[3- or 4-(5-hydroxy-5-methyl-hexyl)-phenyl]-vinyl-phenol,
2-hydroxymethyl-4-{2-[3- or 4-(6-hydroxy-6-methylheptyl)-phenyl]-vinyl}-phenol,
2-hydroxymethyl-4-{2-[3- or 4-(5-hydroxy-5-methylheptyl)-phenyl]-ethyl}-phenol,
2-hydroxymethyl-4-{2-[3- or 4-(6-hydroxy-6-methylheptyl)-phenyl]-ethyl}-phenol,
2-hydroxymethyl-5-(2-[4-(5-hydroxy-5-methyl-hexyl) phenyl]-vinyl-phenol,
6-[3-(3,4-bis-hydroxymethyl-benzyloxy)-phenyl]2-methyl-heptan-2-ol,
4-[3-(5-hydroxy-1,5-dimethyl-hexyl)-phenoxymethyl]2-hydroxymethyl-phenol,
6-[3- or 4-[2-(3,4-bis-hydroxymethyl-phenyl)-vinyl]phenyl}-2-methyl-hexan-2-ol,
7-{4-[2-(3,4-bis-hydroxymethyl-phenyl)-vinyl]phenyl}-2-methyl-heptan-2-ol,
5-{2-[3-(6-hydroxy-6-methyl-heptyl)-phenyl]-1-methyl-vinyl-benzene-1,3-diol,
5-{2-[3-(5-hydroxy-5-methyl-hexyl)-phenyl]-vinyl}benzene-1,3-diol,
5-[3-(6-hydroxy-6-methyl-heptyl)-phenoxymethyl]benzene-1,3-diol,
5-{2-[3-(7-hydroxy-7-methyl-oct-1-enyl)-phenyl]vinyl}-benzene-1,3-diol,
5-{2-[3-(7-hydroxy-7-methyl-octyl)-phenyl]-vinyllbenzene-1,3-diol,
4-{2-[3-(6-hydroxy-6-methyl-heptyl)-phenyl]-vinyl)benzene-1,2-diol,
3-{2-[3-(6-hydroxy-6-methyl-heptyl)-phenyl]-vinyl}phenol,
6-{3-[2-(3,5-bis-hydroxymethyl-phenyl)-vinyl]phenyl}-2-methyl-hexan-2-ol,
3-{2-[3-(7-hydroxy-7-methyl-octyl)-phenyl]-vinyl}phenol,
7-{3-[2-(3,5-bis-hydroxymethyl-phenyl)-vinyl]phenyl-2-methyl-heptan-2-ol,
7-{3-[2-(3,4-bis-hydroxymethyl-phenyl)-vinyl]phenyl}-2-methyl-heptan-2-ol,
7-{3-[2-(4-hydroxymethyl-phenyl)-vinyl]-phenyl}2-methyl-heptan-2-ol,
4-{2-[3-(7-hydroxy-7-methyl-oct-1-enyl)-phenyl]vinyl}-benzene-1,2-diol,
7-[3-(3,4-bis-hydroxymethyl-phenylethynyl)-phenyl]2-methyl-heptan-2-ol,
5-{2-[3-(6-hydroxy-6-methyl-hept-1-enyl)-phenyl)-phenyl]vinyl}-benzene-1,3-diol,
5-{2-[3-(7-ethyl-7-hydroxy-non-1-enyl)-phenyl]vinyl)-benzene-1,3-diol,
5-{2-[3-(7-hydroxy-1-methoxy-1,7-dimethyl-octyl)phenyl]-vinyl}-benzene-1,3-diol,
5-{2-[3-(6-hydroxy-1-methoxy-1,6-dimethyl-heptyl)phenyl]-vinyl}-benzene-1,3-diol,
5-{2-[3-(5-hydroxy-pentyl)-phenyl]-vinyl-benzene-1,3-diol,
5-{2-[3-(5-hydroxy-6-methyl-heptyl)-phenyl]-vinyl}benzene-1,3-diol,
5-{2-[3-(6-hydroxy-7-methyl-octyl)-phenyl]-vinyl)benzene-1,3-diol,
5-{2-[3-(5-hydroxy-6-methyl-hept-1-enyl)-phenyl]vinyl}-benzene-1,3-diol,
5-{2-[3-(6-hydroxy-7-methyl-oct-1-enyl)-phenyl]vinyl}-benzene-1,3-diol,
5-{2-[3-(1,6-dihydroxy-1,6-dimethyl-heptyl)-phenyl]vinyl}-benzene-1,3-diol, and
5-(2-[3-(6-hydroxy-1,6-dimethyl-kept-1-enyl)-phenyl]vinyl}-benzene-1,3-diol.

Vitamin F is a mixture of essential fatty acids, that is, unsaturated acids containing at least one double bond, such as linoleic acid or 9,12-octadecadienoic acid, and its stereoisomers, linolenic acid in a form (9,12,15-octadecatrienoic acid) or γ form (6,9,12-octadecatrienoic acid) and stereoisomers thereof, arachidonic acid or 5,8,11,14-eicosatetraenoic acid and its stereoisomers. Vitamin F or analogues thereof such as mixtures of unsaturated acids containing at least one double bond and especially mixtures of linoleic acid, of linolenic acid and of arachidonic acid, or compounds containing them and especially oils of plant origin containing them such as, for example, jojoba oil, may be used in the cosmetic sheet of the present invention.

V Useful anti-elastase agents include peptide derivatives and especially peptides from leguminous seeds such as those sold by Laboratoires Seriobiologiques de Nancy under the reference Parelastyl; the N-acylamino amide derivatives described in patent application FR-A-2,180,033, such as, for example, ethyl {2-[acetyl(3 trifluoromethylphenyl) amino]-3-methylbutyrylamino}acetate and {2-[acetyl-(3-trifluoromethylphenyl)amino]-3-methylbutyrylamino}acetic acid, and mixtures thereof. Anti-collagenase agents that may be mentioned include metalloprotease inhibitors, such as ethylenediamine acid (EDTA) and cysteine, and mixtures thereof.

VI. Useful protides include proteins (wheat or soybean protein), hydrolysates thereof, for instance those sold by the company Silab under the reference Tensine, and mixtures thereof.

VII. Useful fatty acid derivatives include polyunsaturated phospholipids including the essential fatty acid phospholipids from octopus, and mixtures thereof.

VIII. Useful steroids include DHEA or dehydroepiandrosterone, its biological precursors, its metabolites, and mixtures thereof. The expression "biological precursors" of DHEA especially means A5-pregnenolone, 17α-hydroxy-pregnenolone and 17α-hydroxypregnenolone sulphate. The expression "DHEA derivatives" means both its metabolic derivatives and its chemical derivatives. Metabolic derivatives that may especially be mentioned include Δ5-androstene-3,17-diol and especially 5-androstene-3β, 17.beta-.-diol, Δ4-androstene-3,17-dione, 7-hydroxy DHEA (7α-hydroxy DHEA or 7β-hydroxy DHEA) and 7-keto-DHEA which is itself a metabolite of 7β-hydroxy DHEA. A preferable group is dehydroepiandrosterone, 5-pregnenolone, 17-hydroxypregnenolone, 17-hydroxypregnenolone sulphate, 5-androstene-3,17-diol, 4-androstene-3,17-dione, 7-hydroxy DHEA, 7-hydroxy DHEA, 7-keto-DHEA, and mixtures thereof.

IX. Useful trace elements include copper, zinc, selenium, iron, magnesium and manganese, and mixtures thereof.

X. Useful bleaching agents include any compound for treating or preventing age marks, that is, any depigmenting compound which acts directly on the vitality of the epidermal melanocytes in which melanogenesis takes place and/or which interferes with one of the steps in the biosynthesis of melanin either by inhibiting one of the enzymes involved in melanogenesis or by becoming intercalated as a structural analogue of one of the chemical compounds in the synthetic chain of melanin, the chain of which may thus be blocked and bring about the depigmentation. Bleaching active agents that may be mentioned, for example, include kojic acid and its derivatives, hydroquinone and its derivatives such as arbutin and its esters; ellagic acid and its derivatives; plant extracts, and especially extracts of liquorice, of mulberry or of scutellaria; glutathione and its precursors; cysteine and its precursors; the compounds derived from aminophenol that are described in document WO-A-99/10318, such as, especially, N-ethyloxycarbonyl-4-aminophenol, N-ethyloxycarbonyl-O-ethyloxy carbonyl-4-aminophenol, N-cholesteryloxycarbonyl-4-aminophenol and N-ethylaminocarbonyl-4-aminophenol; and mixtures of these compounds.

XI. Useful extracts of algae include extracts of red or brown algae and, for example, the extract of brown algae from the Laminaria family, for instance the extracts from the species *Laminaria digitata*, and more particularly the product sold by the company CODIF under the name Phycosaccharides, which is a concentrated solution of an oligosaccharide obtained by controlled enzymatic depolymerization of membrane polysaccharides of a brown alga. It comprises a sequence of two uric acids: mannuronic acid and guluronic acid.

XII. Useful extracts of planktons include plankton in aqueous dispersion (CTFA name: *Vitreoscilla* Ferment) sold under the name Mexoryl SAH by the company Chimex.

XIII. Useful enzymes that may be used include any enzyme of animal, microbiological (bacterial, fungal or viral) or synthetic origin (obtained by chemical or biotechnological synthesis), in pure crystalline form or in a form diluted in an inert diluent. Examples that may be mentioned are from among lipases, proteases, phospholipases, cellulases, peroxidases and especially lactoperoxidases, catalases and superoxide dismutases, or from among plant extracts containing the abovementioned enzymes, and mixtures thereof. They may be selected, for example, from the product sold under the trade name "Subtilisine SP 554" by the company Novo Nordisk and from the product sold under the trade name "Lysoveg LS" by the company Laboratoires Serobiologiques de Nancy. Coenzymes that may especially be used include ubiquinone or coenzyme Q10, which belongs to the family of alkylenated-chain benzoquinones, coenzyme R, which is biotin (or vitamin H), and mixtures thereof.

XIV. Useful flavonoids that may be mentioned, for example, include isoflavonoids, which constitute a subclass of flavonoids, formed from a 3-phenylchroman skeleton which may comprise varied substituents and different levels of oxidation. The term "isoflavonoid" combines several classes of compounds, among which mention may be made of isoflavones, isoflavanones, rotenoids, pterocarpans, isoflavans, isoflavan-3-enes, 3-arylcoumarins, 3-aryl-4-hydroxycoumarins, coumestanes, coumaronochromones, a-methyldeoxybenzoins and 2-arylbenzofurans, and mixtures thereof. In this regard, reference will advantageously be made, for a complete review of isoflavonoids, their methods of analysis and their sources, to chapter 5 "Isoflavonoids" written by P. M. Dewick in The Flavonoids, edited by Harbone, pp. 125-157 (1988).

The isoflavonoids may be of natural or synthetic origin. The expression "natural origin" means an isoflavonoid in pure form or dissolved to various concentrations, obtained by various extraction processes from an element, generally a plant, of natural origin. The expression "synthetic origin" means an isoflavonoid in pure form or dissolved to various concentrations, obtained by chemical synthesis. Isoflavonoids of natural origin are preferably used. Among these, mention may be made of: daidzin, genistin, daidzein, formononetin, cuneatin, genistein, isoprunetin and prunetin, cajanin, orobol, pratensein, santal, junipegenin A, glycitein, afrormosin, retusin, tectorigenin, irisolidone and jamaicin, and also analogues and metabolites thereof.

XV. Useful ceramides that may be used include any type of ceramide of natural or synthetic origin, for example of type II, of type III, of type IV, of type V or of type VI, and mixtures thereof. Examples of ceramides that may be mentioned include N-oleoyldihydrosphingosine, N-stearoylphytosphingosine, N-α-hydroxybehenoyldihydrosphingosine, N-α-hydroxypalmitoyldi-hydrosphingosine, N-linoleoyldihydrosphingosine, N-palmitoyldihydrosphingosine, N-stearoyldihydrosphingosine and N-behenoyldihydrosphingosine, and mixtures thereof.

Mention may also be made of the product consisting of a mixture of glycoceramides, sold under the trade name Glycocer by the company Waitaki International Biosciences; the compounds described in documents EP-A-0 227 994 and WO-A-94/07844, such as, for example, Questamide H (bis(N-hydroxyethyl-Ncetyl)malonamide) sold by the company Quest, cetylic acid N-(2-hydroxyethyl)-N-(3-cetyloxy-2-hydroxypropyl)amide; N-docosanoyl-N-methyl-D-glucamine described in patent application WO-A-92/05764. Mixtures of these ceramides may also be used.

As examples of the whitening agent, mention may be made of ascorbic acid or derivatives thereof, kojic acid or derivatives thereof, tranexamic acid or derivatives thereof, resorcinol or derivatives thereof, alkoxysalicylic acid or salts thereof, adenosine phosphate or salts thereof, hydroquinone or glycosides thereof or derivatives thereof, glutathione, 4-(4-hydroxyphenyl)-2-butanol, magnolignan (5,5'-dipropyl-biphenyl-2,2'-diol), placenta extracts, *chamomilla recutita*, and the like.

Ascorbic acid has a D-configuration or L-configuration, and the L-configuration one is preferably employed. Ascorbic acid is also referred to as vitamin C, and has effects of inhibiting the production of melanin due to the strong reduction effects of ascorbic acid. The derivatives of ascorbic acid may be salts of ascorbic acid, and the salts of ascorbic acid are preferably selected from sodium ascorbate, magnesium ascorbyl phosphate, and sodium ascorbyl phosphate. The derivatives of ascorbic acids may be glycosides of ascorbic acid or esters of ascorbic acid. As an example of glycosides of ascorbic acid, mention may be made of, for example, ascorbyl glucoside. As examples of esters of ascorbic acid, mention may be made of, for example, silyl ascorbate, tocopheryl ascorbate, and alkyl ascorbate. As the alkyl ascorbate, methyl ascorbate or ethyl ascorbate is preferably used. In particular, ascorbyl glucoside is preferable. Ascorbic acid or derivatives thereof can be used alone or in combination with two or more types thereof.

As detailed examples of derivatives of ascorbic acid, mention may be made of, for example, 5,6-di-O-dimethylsilyl ascorbate, which is commercially available as PRO-AA from Exsymol SAM; dl-alpha-tocopheryl-2-l-ascorbyl phosphate which is commercially available as SEPIVITAL EPC from Senju Pharmaceutical Co., Ltd.; sodium ascorbyl phosphate which is commercially available as Stay-C 50 from Roche; ascorbyl glucoside which is commercially available from Hayashibara Biochemical Labs., Inc.; 3-O-ethyl ascorbic acid; and the like.

Ascorbic acid or the derivative thereof is preferably used in combination with a copolymer of styrene and maleic anhydride. In particular, at least one part of the maleic anhydride unit of the aforementioned copolymer is preferably hydrolyzed. The aforementioned hydrolyzed maleic anhydride unit may be in the form of an alkaline salt such as a sodium salt, a potassium salt, a lithium salt, or the like. The aforementioned maleic anhydride unit preferably occupies 0.4 to 0.9 mol per one mol of the entire copolymer, and a ratio of the maleic anhydride unit and the styrene unit is preferably 50:50. In particular, it is preferable that the ratio of the maleic anhydride unit and the styrene unit be preferably 50:50, and the ammonium salt or sodium salt be used. By employing ascorbic acid or the derivative thereof in combination with the aforementioned copolymer, stability of ascorbic acid or the derivative thereof is improved. As the aforementioned copolymer, for example, a copolymer of styrene and maleic anhydride (50/50) in the form of an ammonium salt in a concentration of 30% in water, which is commercially available as product number SMA 1000 H (trademark) from Atofina Chemicals Inc.; or a copolymer of styrene and maleic anhydride (50/50) in the form of a sodium salt in a concentration of 40% in water, which is commercially available as product number SMA 1000 H Na (trademark) from Atofina Chemicals Inc., can be used. The aforementioned copolymer is used in a concentration ranging from 0.1 to 20% by weight, and preferably ranging from 0.1 to 10% by weight, with respect to the total weight of the whitening agent for topical application.

As an example of derivatives of kojic acid, mention may be made of, for example, kojic acid glucoside.

As examples of derivatives of tranexamic acid, mention may be made of dimers of tranexamic acid (such as hydrochloric acid trans-4-(trans-aminomethylcyclohexanecarbonyl)aminomethylcyclohexane carboxylic acid), esters of tranexamic acid and hydroquinone (such as 4'-hydroxyphenyl trans-4-aminomethylcyclohexane carboxylate), esters of tranexamic acid and gentisic acid (such as 2-(trans-4-aminomethylcyclohexanecarbonyloxy)-5-hydroxybenzoic acid and salts thereof), tranexamic amides (such as trans-4-aminomethylcyclohexanecarboxylic acid methylamide and salts thereof, trans-4-(p-methoxybenzoyl)aminomethylcyclohexane carboxylic acid and salts thereof, and trans-4-guanidinomethylcyclohexane carboxylic acid and salts thereof), and the like.

As examples of derivatives of resorcinol, mention may be made of, for example, 4-n-butylresorcinol (Rucinol) and the like.

An alkoxysalicylic acid is a compound in which any one of hydrogen atoms in the 3-position, the 4-position, or the 5-position of salicylic acid is substituted by an alkoxy group. The aforementioned alkoxy group is preferably any one of a methoxy group, an ethoxy group, a propoxy group, an isopropoxy group, a butoxy group, and isobutoxy group, and is more preferably a methoxy group or an ethoxy group. As examples of the compound, mention may be made of, for example, 3-methoxysalicylic acid, 3-ethoxysalicylic acid, 4-methoxysalicylic acid, 4-ethoxysalicylic acid, 4-propoxysalicylic acid, 4-isopropoxysalicylic acid, 4-butoxysalicylic acid, 5-methoxysalicylic acid, 5-ethoxysalicylic acid, 5-propoxysalicylic acid, and the like. Salts of the alkoxysalicylic acids are not particularly limited. As examples thereof, mention may be made of, for example, alkali metal salts or alkaline earth metal salts such as sodium salts, potassium salts, calcium salts, and the like, ammonium salts, amino acid salts, and the like. A potassium salt of 4-methoxysalicylic acid is preferable.

As examples of adenosine phosphate or salts thereof, mention may be made of, for example, disodium adenosine phosphate, and the like.

As examples of glycosides of hydroquinone, mention may be made of, for example, hexose glycosides such as hydroquinone alpha-D-glucose, hydroquinone beta-D-glucose, hydroquinone alpha-L-glucose, hydroquinone beta-L-glucose, hydroquinone alpha-D-galactose, hydroquinone beta-D-galactose, hydroquinone alpha-L-galactose, hydroquinone beta-L-galactose, and the like; pentose glycosides such as hydroquinone alpha-D-ribose, hydroquinone beta-D-ribose, hydroquinone alpha-L-ribose, hydroquinone beta-L-ribose, hydroquinone alpha-D-arabinose, hydroquinone beta-D-arabinose, hydroquinone alpha-L-arabinose, hydroquinone beta-L-arabinose, and the like; aminosugar glycosides such as hydroquinone alpha-D-glucosamine, hydroquinone beta-D-glucosamine, hydroquinone alpha-L-glucosamine, hydroquinone beta-L-glucosamine, hydroquinone alpha-D-galactosamine, hydroquinone beta- D-galactosamine, hydroquinone alpha-L-galactosamine, hydroquinone beta-L-galactosamine, and the like; urocanic acid glycosides such as hydroquinone alpha-D-glucuronic acid, hydroquinone beta-D-glucuronic acid, hydroquinone alpha-L-glucuronic acid, hydroquinone beta-L-glucuronic acid, hydroquinone alpha-D-galacturonic acid, hydroquinone beta-D-galacturonic acid, hydroquinone alpha-L-galacturonic acid, hydroquinone beta-L-galacturonic acid, and the like; and the like. Among these compounds, hydroquinone beta-D-glucose (hereinafter, referred to as "arbutin") is preferable. As examples of derivatives of hydroquinone or glycosides thereof, mention may be made of, for example, salts of hydroquinone or glycosides thereof. In particular, as examples of arbutin derivatives, mention may be made of, for example, 6-O-caffeoylarbutin, and the like.

As the whitening active ingredients, in particular, L-ascorbic acid or derivatives thereof, kojic acid or derivatives thereof, tranexamic acid or derivatives thereof, arbutin or derivatives thereof, and Rucinol are preferable, and ascorbic acid derivatives such as 3-O-ethyl L-ascorbic acid and L-ascorbic acid glucoside are more preferable.

The self-standing cosmetic sheet according to the present invention may comprise the cosmetic active ingredient(s) in an amount of from 0.01 to 30% by weight, preferably from 0.05 to 20% by weight, and more preferably from 0.1 to 10% by weight, relative to the total weight of the cosmetic sheet.

The cosmetic sheet according to the present invention may comprise, in addition to the aforementioned components, components typically employed in cosmetics, specifically, such as acids, bases, salts, pigments, powders, surfactants, oils, organic solvents, silicones, silicone derivatives, natural extracts derived from animals or vegetables, waxes, and the like, within a range which does not impair the effects of the present invention.

The self-standing cosmetic sheet according to the present invention may be attached to a substrate sheet. The materials for the substrate are not limited. Two or more materials may be used in combination. Thus, a single type of material or a combination of different types of materials may be used. In any event, it is preferable that the substrate sheet be flexible or elastic.

It is more preferable that the substrate be water-soluble, because it is possible to leave the cosmetic sheet according to the present invention by washing the substrate with water, if the cosmetic sheet is hydrophobic. In fact, as mentioned above, a combination of a cationic polymer and an anionic polymer can form a hydrophobic sheet. Therefore, a combination of a water-soluble substrate sheet and a cosmetic sheet according to the present invention comprising at least one biocompatible and/or biodegradable hydrophobic polymer comprising at least one cationic polymer and at least one anionic polymer is preferable. As examples of the water-soluble materials, mention may be made of poly(meth) acrylic acids, polyethyleneglycols, polyacrylamides, polyvinylalcohol (PVA), starch, celluloseacetates, and the like. PVA is preferable.

The substrate sheet may have a thickness of more than that of the cosmetic sheet according to the present invention, in order to ease the handling of the cosmetic sheet attached to the substrate sheet. The thickness of the substrate sheet is not limited, but may be from 1 μm to 5 mm, preferably from 10 μm to 1 mm, and more preferably from 50 to 500 μm.

It is more preferable that the cosmetic sheet be releasable from the substrate sheet. The mode of release is not limited. Therefore, the cosmetic sheet may be peeled from the substrate sheet, or released by the dissolution of the substrate sheet into a solvent such as water.

The self-standing cosmetic sheet according to the present invention is used for cosmetic treatments for the skin, in particular the face. The self-standing cosmetic sheet according to the present invention can be in any shape or form. For example, it can be used as a full-face mask sheet, or a patch for a part of the face such as the cheek, nose, and around the eyes.

The second embodiment according to the present invention is a cosmetic process for treating the aging of the skin, absorbing sebum on the skin, controlling the perspiration on the skin, controlling odors on the skin, and/or delivering at least one cosmetic active ingredient via the skin, comprising the step of applying onto the skin the self-standing cosmetic sheet which is the same as that used in the first embodiment according to the present invention, provided that it comprises at least one cosmetic active ingredient as described above.

In particular, the present invention can deliver a cosmetic active ingredient or ingredients to the skin or via the skin. A high concentration of cosmetic active ingredient(s) can be incorporated in the cosmetic sheet according to the present invention, and can be kept inside the sheet because the sheet is self-standing. Therefore, by applying the cosmetic sheet according to the present invention onto the target area on the skin, the cosmetic active ingredient(s) can be delivered to or via the skin for a long time.

Since the cosmetic sheet according to the present invention have a very thin thickness of from 10 to 1000 nm, preferably from 30 to 500 nm, more preferably from 50 to 300 nm, even more preferably from 70 to 200 nm, and most preferably from 80 to 150 nm, the cosmetic active ingredient(s) in the sheet can easily diffuse into the skin. As a result, the effective penetration of the cosmetic active ingredient(s) to the skin can be realized.

The above cosmetic effects can be adjusted or controlled by changing the chemical composition, the thickness and/or the surface roughness of the cosmetic sheet according to the present invention, as well as by changing the type and/or amount of a cosmetic active ingredient.

It is also possible to apply a makeup cosmetic composition onto the cosmetic sheet according to the present invention after being applied onto the skin.

It is preferable that the self-standing cosmetic sheet according to the present invention be used under the conditions whereby it is attached to a substrate sheet, because the application of the cosmetic sheet to the skin becomes easier. For example, the composite sheet of the cosmetic sheet according to the present invention and the substrate sheet can be applied onto the skin such that the cosmetic sheet directly touches the skin, and the substrate sheet can be removed by peeling off from the cosmetic sheet or washed with water if the cosmetic sheet is hydrophobic and the substrate sheet is water-soluble. Thus, the cosmetic sheet alone according to the present invention can be left on the skin.

EXAMPLES

The present invention will be described in more detail by way of examples, which however should not be construed as limiting the scope of the present invention.

Example 1

An aqueous solution of chitosan (1 mg/mL, 1% (v/v) acetic acid) and an aqueous solution of sodium alginate (1 mg/mL, 0.5 M NaCl) were prepared with deionized water.

A multi-layered nanosheet composed of chitosan and sodium alginate was prepared by the following steps:

(1) forming a chitosan layer by dropping 1 mL of the aqueous solution of chitosan on the surface of the $SiO_2$ substrate, followed by rotating the substrate at 4,500 rpm for 20 seconds, and rinsing twice with deionized water and drying by spinning the support for 30 seconds;

(2) forming a sodium alginate layer by dropping 1 mL of the aqueous solution of sodium alginate on the surface of the $SiO_2$ substrate coated by the chitosan layer, followed by rotating the substrate at 4,500 rpm for 20 seconds, and rinsing twice with deionized water and drying by spinning the support by 30 seconds;

(3) repeating the above formation of the chitosan and sodium alginate layers by the spin-coating-assisted layer-by-layer method (4,500 rpm, 15 seconds) to attain a desired thickness of the nanosheet;

(4) terminating the spin-coating-assisted layer-by-layer method at the chitosan layer forming stage, and drying the surface of the chitosan layer by nitrogen;

(5) casting a 10 wt % polyvinylalcohol (PVA) aqueous solution on the multi-layered nanosheet, leaving the solution for 12 hours, and drying to form a PVA substrate sheet; and (6) peeling the multi-layered nanosheet (2.0*2.0 cm$^2$) with the PVA substrate sheet having a thickness of 70 μm from the $SiO_2$ support using tweezers.

The thickness of the multi-layered nanosheet composed of chitosan and sodium alginate was about 90 nm. The thickness of the nanosheet was determined by the cross-sectional analysis of the nanosheet edge using atomic force microscopy (AFM).

[Evaluation 1]

A cosmetic sheet, which was composed of the multi-layered nanosheet and the PVA substrate sheet, according to Example 1 was evaluated as to visibility on the skin, feel to touch of the skin, ability of pore hiding on the skin, and skin protection.

(Visibility on Skin)

The cosmetic sheet according to Example 1 was applied on the cheek of an adult woman, and the PVA substrate sheet was dissolved with water. On the first multi-layered nanosheet on the cheek, a second cosmetic sheet was applied, and the PVA substrate sheet was dissolved with water. By repeating this once more, the three layers of the nanosheets were made on the cheek of the adult woman.

Each time of forming one layer of the nanosheet on the cheek, the visibility of the nanosheet was evaluated. This was performed by 5 adult women, and the visibility was ranked as A (hard to be recognized by 3 or more women), B (hard to be recognized by 2 women) and C (hard to be recognized by one woman or less).

As a control, a commercial cosmetic auxiliary patch film (Design Tape marketed by Kazuki International Corporation) according to WO 2009/041121 was used. A single film of the film was applied on the cheek of 5 adult women, the visibility of the film was evaluated as above.

The results are shown in Table 1.

TABLE 1

|  | Visibility |
| --- | --- |
| 1 layer of the nanosheet | A |
| 2 layers of the nanosheets | A |
| 3 layers of the nanosheets | A |
| Control | C |

It was found that the nanosheet was invisible even if a plurality of the nanosheets were applied on the skin. On the other hand, the control was visible.

In addition, the nanosheet caused no skin irritation, while the control caused some irritation.

(Feel to Touch on Skin)

The cosmetic sheet according to Example 1 was applied on the cheek of an adult woman, and the PVA substrate sheet was dissolved with water. On the first multi-layered nanosheet on the cheek, a second cosmetic sheet was applied, and the PVA substrate sheet was dissolved with water. By repeating this once more, the three layers of the nanosheets were made on the cheek of the adult woman.

Each time of forming one layer of the nanosheet on the cheek, the feel to the touch of the skin, to which the nanosheet had been applied, was evaluated. This was performed by 5 adult women, and the feel to the touch of the skin was ranked as A (smooth for 3 or more women), B (smooth for 2 women) and C (smooth for one woman or less).

As a control, a commercial cosmetic auxiliary patch film (Design Tape marketed by Kazuki International Corporation) according to WO 2009/041121 was used. A single film of the film was applied on the cheek of 5 adult women, the feel to the touch of the skin was evaluated as above.

The results are shown in Table 2.

TABLE 2

|  | Feel to Touch of Skin |
| --- | --- |
| 1 layer of the nanosheet | A |
| 2 layers of the nanosheets | A |
| 3 layers of the nanosheets | A |
| Control | C |

It was found that the nanosheet provides a very smooth feel to the touch of the skin. On the other hand, the control was difficult to provide smooth feel to the touch of the skin.

(Pore Hiding)

The cosmetic sheet according to Example 1 was applied on the cheek of an adult woman, and the PVA substrate sheet was dissolved with water. On the first multi-layered nanosheet on the cheek, a second cosmetic sheet was applied, and the PVA substrate sheet was dissolved with water. By repeating this once more, the three layers of the nanosheets were made on the cheek of the adult woman.

Each time of forming one layer of the nanosheet on the cheek, the pore hiding ability thereof was evaluated. This was performed by 5 adult women, and the pore hiding ability was ranked as A (hard to be recognized by 3 or more women), B (hard to be recognized by 2 women) and C (hard to be recognized by one woman or less).

As a control, the above evaluation was performed without the nanosheet.

The results are shown in Table 3.

TABLE 3

|  | Pore Hiding Ability |
| --- | --- |
| 1 layer of the nanosheet | B |
| 2 layers of the nanosheets | A |
| 3 layers of the nanosheets | A |
| Control | C |

It was found that even a single nanosheet had pore hiding effects, and that the pore hiding effects increased in accordance with the number of the nanosheet layers.

(Skin Protection)

The cosmetic sheet according to Example 1 was applied on the cheek of an adult woman, and the PVA substrate sheet was dissolved with water. On the first multi-layered nanosheet on the cheek, a second cosmetic sheet was applied, and the PVA substrate sheet was dissolved with water. By repeating this once more, the three layers of the nanosheets were made on the cheek of the adult woman.

Each time of forming one layer of the nanosheet on the cheek, the skin protection ability thereof was evaluated as follows.

A powder of carbon black was applied on the nanosheet which had been applied onto the skin. After removing the carbon black particles by washing the nanosheet with water, the color or darkness of the nanosheet was evaluated. This was performed by 5 adult women, and the skin protection ability was ranked as A (clean for 3 or more women), B (clean for 2 women) and C (clean for one woman or less).

As a control, the above evaluation was performed without the nanosheet. Thus, a powder of carbon black was applied directly on the skin. After removing the carbon black particles by washing the skin with water, the color or darkness of the nanosheet was evaluated as above.

The results are shown in Table 4.

TABLE 4

|  | Skin Protection |
| --- | --- |
| 1 layer of the nanosheet | A |
| 2 layers of the nanosheets | A |
| 3 layers of the nanosheets | A |
| Control | C |

It was found that even a single nanosheet had skin protection effects, and that the skin protection effects increased in accordance with the number of the nanosheet layers.

Example 2

An aqueous solution of chitosan (1 mg/mL, 1% (v/v) acetic acid) and beta-cyclodextrin (0.2 mg/mL) and an aqueous solution of sodium alginate (1 mg/mL, 0.5 M NaCl) and beta-cyclodextrin (0.2 mg/mL) were prepared with deionized water.

A multi-layered nanosheet composed of chitosan, sodium alginate, and beta-cyclodextrin was prepared in the following steps:

(1) forming a chitosan+beta-cyclodextrin layer by dropping 1 mL of the aqueous solution of chitosan and beta-cyclodextrin on the surface of the $SiO_2$ substrate, followed by rotating the substrate at 4,500 rpm for 20 seconds, and rinsing twice with deionized water and drying by spinning the support for 30 seconds;

(2) forming a sodium alginate+beta-cyclodextrin layer by dropping 1 mL of the aqueous solution of sodium alginate and beta-cyclodextrin on the surface of the $SiO_2$ substrate coated by the chitosan+beta-cyclodextrin layer, followed by rotating the substrate at 4,500 rpm for 20 seconds, and rinsing twice with deionized water and drying by spinning the support by 30 seconds;

(3) repeating the above formation of the chitosan+beta-cyclodextrin and sodium alginate+beta-cyclodextrin layers by the spin-coating-assisted layer-by-layer method (4,500 rpm, 15 seconds) to attain a desired thickness of the nanosheet;

(4) terminating the spin-coating-assisted layer-by-layer method at the chitosan+beta-cyclodextrin layer forming stage, and drying the surface of the chitosan+beta-cyclodextrin layer by nitrogen;

(5) casting a 10 wt % polyvinylalcohol (PVA) aqueous solution on the multi-layered nanosheet, leaving the solution for 12 hours, and drying to form a PVA substrate sheet; and (6) peeling the multi-layered nanosheet (2.0*2.0 cm$^2$) with the PVA substrate sheet having a thickness of 70 μm from the $SiO_2$ support using tweezers.

The thickness of the multi-layered nanosheet composed of chitosan, sodium alginate, and beta-cyclodextrin was about 100 nm. The thickness of the nanosheet was determined by the cross-sectional analysis of the nanosheet edge using atomic force microscopy (AFM).

The amount of beta-cyclodextrin in the nanosheet (chitosan and sodium alginate) was determined by an HPLC method, and found to be about 10 wt %.

[Evaluation 2]

Two cosmetic sheets, which were composed of the multi-layered nanosheet and the PVA substrate sheet, according to Examples 1 and 2 were evaluated as to the ability of controlling malodor associated with perspiration on the axilla.

Each of the cosmetic sheets (2.0*2.0 cm$^2$) according to Examples 1 and 2 was applied on the underarm of an adult man, and the PVA substrate sheet was dissolved with water. After 6 hours, the smell of the underarm was evaluated. This was performed for 5 adult men, and the malodor controlling ability was ranked as A (not smelling), B (smelling slightly) and C (smelling strongly).

As a control, the above evaluation was performed without the cosmetic sheet.

The results are shown in Table 5.

TABLE 5

|  | Malodor Control |
| --- | --- |
| Example 1 | B |
| Example 2 | A |
| Control | C |

It was found that the cosmetic sheets according to Examples 1 and 2, in particular Example 2, were effective in reducing or removing perspiration malodor.

In addition, the cosmetic sheets according to Examples 1 and 2 caused no skin irritation.

Example 3

An aqueous solution of chitosan (1 mg/mL, 1% (v/v) acetic acid) and 3-O-ethyl ascorbic acid (0.2 mg/mL) and an aqueous solution of sodium alginate (1 mg/mL, 0.5 M NaCl) and 3-O-ethyl ascorbic acid (0.2 mg/mL) were prepared with deionized water.

A multi-layered nanosheet composed of chitosan, sodium alginate, and 3-O-ethyl ascorbic acid was prepared in the following steps:
(1) forming a chitosan+3-O-ethyl ascorbic acid layer by dropping 1 mL of the aqueous solution of chitosan and 3-O-ethyl ascorbic acid on the surface of the $SiO_2$ substrate, followed by rotating the substrate at 4,500 rpm for 20 seconds, and rinsing twice with deionized water and drying by spinning the support for 30 seconds;
(2) forming a sodium alginate+3-O-ethyl ascorbic acid layer by dropping 1 mL of the aqueous solution of sodium alginate and 3-O-ethyl ascorbic acid on the surface of the $SiO_2$ substrate coated by the chitosan+3-O-ethyl ascorbic acid layer, followed by rotating the substrate at 4,500 rpm for 20 seconds, and rinsing twice with deionized water and drying by spinning the support by 30 seconds;
(3) repeating the above formation of the chitosan+3-O-ethyl ascorbic acid and sodium alginate+3-O-ethyl ascorbic acid layers by the spin-coating-assisted layer-by-layer method (4,500 rpm, 15 seconds) to attain a desired thickness of the nanosheet;
(4) terminating the spin-coating-assisted layer-by-layer method at the chitosan+3-O-ethyl ascorbic acid layer forming stage, and drying the surface of the chitosan+3-O-ethyl ascorbic acid layer by nitrogen;
(5) casting a 10 wt % polyvinylalcohol (PVA) aqueous solution on the multi-layered nanosheet, leaving the solution for 12 hours, and drying to form a PVA substrate sheet; and
(6) peeling the multi-layered nanosheet (2.0*2.0 cm$^2$) with the PVA substrate sheet having a thickness of 70 μm from the $SiO_2$ support using tweezers.

The thickness of the multi-layered nanosheet composed of chitosan, sodium alginate, and 3-O-ethyl ascorbic acid was about 100 nm. The thickness of the nanosheet was determined by the cross-sectional analysis of the nanosheet edge using atomic force microscopy (AFM).

The amount of 3-O-ethyl ascorbic acid in the nanosheet (chitosan and sodium alginate) was determined by an HPLC method, and found to be about 10 wt %.

[Evaluation 3]

Two cosmetic sheets, which were composed of the multi-layered nanosheet and the PVA substrate sheet, according to Examples 1 and 3, were evaluated as to their ability of whitening the skin.

Each of the cosmetic sheets (2.0*2.0 cm$^2$) according to Examples 1 and 3 was applied on the lower arm of an adult, and the PVA substrate sheet was dissolved with water. Then, UVB light with an intensity of about 2-times the minimum erythema dose was irradiated onto the nanosheet to induce skin darkening. This was performed for 10 men and 10 women, and was repeated for 4 weeks.

After 4 weeks, the color of the skin was measured with a colorimeter (SPECTRO PHOTOMETER, CMS-35FS, Murakami Color Research Laboratory). Specifically, the colorimeter was used to determine the color contrast of the skin, thus evaluating the effects of the nanosheet. The L* value was measured and used as an index of the color contrast of the skin. The difference of the L* value (ΔL*) in the skin color between before and after the 4 weeks (ΔL*=L* after the 4 weeks−L* before the 4 weeks) was calculated based on the measured L* values.

As a result, it was found that the ΔL* for the cosmetic sheet according to Example 3 was smaller than that for the cosmetic sheet according to Example 1. Therefore, it was recognized that the use of the cosmetic sheet according to Example 3 reduced the pigmentation of the skin.

In addition, the cosmetic sheets according to Examples 1 and 3 caused no skin irritation.

The invention claimed is:

1. A process for controlling perspiration and/or odors on the skin, the process comprising:
adhering onto the skin a cosmetic sheet comprising:
(a) a film comprising at least one biocompatible and/or biodegradable hydrophobic polymer layer comprising at least one cationic polymer, at least one anionic polymer, and at least one anti-perspirant agent and/or deodorant agent, and
(b) at least one water-soluble substrate, and
removing the (b) at least one water-soluble substrate,
wherein the film (a) has a thickness ranging from 80 nm to 150 nm,
wherein the at least one anti-perspirant agent and/or deodorant agent is present in the film (a) in an amount ranging from about 0.01% to about 30% by weight, relative to the total weight of the film (a), and
wherein the at least one anit-perspirant agent and/or deodorant agent is incorporated inside the at least one biocompatible and/or biodegradable hydrophobic polymer layer of the film (a).

2. The process according to claim 1, wherein the biocompatible and/or biodegradable hydrophobic polymer layer is non-cross-linked.

3. The process according to claim 1, wherein the at least one cationic polymer has at least one positively chargeable moiety chosen from quaternary ammonium groups, guanidine groups, biguanide groups, imidazole groups, imino groups, pyridyl groups, or amino groups.

4. The process according to claim 3, wherein the at least one cationic polymer is chosen from chitosan, collagen, polyallylamines, polyvinylamines, polydiallyldialkyl ammonium chloride, polyanilines, polyvinylimidazoles, polydimethylaminoethylenemethacrylates, poly-1-methyl-2-vinylpyridine, polyamines, polyimines, polyethyleneimines, polyvinylpyridines, poly(quaternary pyridine), polylysines, polyornithines, polyarginines, polyhistidines, polyaminopropyl biguanides, or salts thereof.

5. The cosmetic process according to claim 1, wherein the at least one anionic polymer has at least one negatively chargeable moiety chosen from sulfuric groups, sulfate groups, sulfonic groups, sulfonate groups, phosphoric groups, phosphate groups, phosphonic groups, phosphonate groups, carboxylic groups, or carboxylate groups.

6. The process according to claim 5, wherein the at least one anionic polymer is chosen from alginic acid, hyaluronic acid, polyglutamic acids, polylactic acids, polyglycolic acids, polycaprolactones, poly(meth)acrylic acids, polyamic acids, polystyrene sulfonate, poly(vinyl sulfate), dextran sulfate, chondroitin sulfate, polymaleic acids, polyfumaric acids, carboxy methyl cellulose, styrene maleic anhydride derivatives, or salts thereof.

7. The process according to claim 1, wherein the at least one antiperspirant agent and/or deodorant agent is present in the film (a) in an amount ranging from about 0.05% to about 20% by weight, relative to the total weight of the film (a).

8. The process according to claim 1, wherein the at least one antiperspirant agent and/or deodorant agent is present in the film (a) in an amount ranging from about 0.1% to about 10% by weight, relative to the total weight of the film (a).

9. An adhesive cosmetic sheet for the skin, comprising:
(a) a film comprising at least one biocompatible and/or biodegradable hydrophobic polymer layer comprising at least one cationic polymer, at least one anionic polymer, and at least one antiperspirant agent and/or deodorant agent; and
(b) at least one water-soluble substrate,
wherein the film (a) has a thickness ranging from 80 nm to 150 nm,
wherein the at least one anti-perspirant agent and/or deodorant agent is present in the film (a) in an amount ranging from about 0.01% to about 30% by weight, relative to the total weight of the film (a), and
wherein the at least one anti-perspirant agent and/or deodorant agent is incorporated inside the at least one biocompatible and/or biodegradable hydrophobic polymer layer of the film (a).

10. The adhesive cosmetic sheet according to claim 9,
wherein the at least one cationic polymer is chosen from chitosan, collagen, polyallylamines, polyvinylamines, polydiallyldialkyl ammonium chloride, polyanilines, polyvinylimidazoles, polydimethylaminoethylenemethacrylates, poly-1-methyl-2-vinylpyridine, polyamines, polyimines, polyethyleneimines, poyvinylpyridines, poly(quaternary pyridine), polylysines, polyornithines, polyarginines, polyhistidines, polyaminopropyl biguanides, or salts thereof; and
wherein the at least one anionic polymer is chosen from alginic acid, hyaluronic acid, polyglutamic acids, polylactic acids, polyglycolic acids, polycaprolactones, poly(meth)acrylic acids, polyamic acids, polystyrene sulfonate, poly(vinyl sulfate), dextran sulfate, chondroitin sulfate, polymaleic acids, polyfumaric acids, carboxy methyl cellulose, styrene maleic anhydride derivatives, or salts thereof.

11. The adhesive cosmetic sheet according to claim 9, wherein the at least one biocompatible and/or biodegradable hydrophobic polymer layer is non-cross-linked.

12. The adhesive cosmetic sheet according to claim 9, wherein the at least one antiperspirant agent and/or deodorant agent is present in the film (a) in an amount ranging from about 0.05% to about 20% by weight, relative to the total weight of the film (a).

13. The adhesive cosmetic sheet according to claim 9, wherein the at least one antiperspirant agent and/or deodorant agent is present in the film (a) in an amount ranging from about 0.1% to about 10% by weight, relative to the total weight of the film (a).

14. The adhesive cosmetic sheet according to claim 9, wherein the at least one antiperspirant agent and/or deodorant agent is chosen from cyclodextrins.

15. The adhesive cosmetic sheet according to claim 9, wherein the at least one antiperspirant agent and/or deodorant agent is chosen from antibacterial agents.

16. The process according to claim 1, wherein the at least one antiperspirant agent and/or deodorant agent is chosen from cyclodextrins.

17. The process according to claim 1, wherein the at least one antiperspirant agent and/or deodorant agent is chosen from antibacterial agents.

18. A process for whitening the skin, the process comprising:
adhering onto the skin a cosmetic sheet comprising:
(a) a film comprising at least one biocompatible and/or biodegradable hydrophobic polymer layer comprising at least one cationic polymer, at least one anionic polymer, and at least one skin whitening agent, and
(b) at least one water-soluble substrate, and
removing the (b) at least one water-soluble substrate,
wherein the film (a) has a thickness ranging from 80 nm to 150 nm,
wherein the at least one skin whitening agent is present in the film (a) in an amount ranging from about 0.01% to about 30% by weight, relative to the total weight of the film (a), and
wherein the at least one skin whitening agent is incorporated inside the at least one biocompatible and/or biodegradable hydrophobic polymer layer of the film (a).

19. A process for absorbing sebum on the skin, the process comprising:
adhering onto the skin a cosmetic sheet comprising:
(a) a film comprising at least one biocompatible and/or biodegradable hydrophobic polymer layer comprising at least one cationic polymer, at least one anionic polymer, and at least one anti-sebum agent, and
(b) at least one water-soluble substrate, and
removing the (b) at least one water-soluble substrate,
wherein the film (a) has a thickness ranging from 80 nm to 150 nm,
wherein the at least one anti-sebum agent is present in the film (a) in an amount ranging from about 0.01% to about 30% by weight, relative to the total weight of the film (a), and
wherein the at least one anti-sebum agent is incorporated inside the at least one biocompatible and/or biodegradable hydrophobic polymer layer of the film (a).

20. A process for treating and/or preventing acne on skin, the process comprising:
adhering onto the skin a cosmetic sheet comprising:
(a) a film comprising at least one biocompatible and/or biodegradable hydrophobic polymer layer comprising at least one cationic polymer, at least one anionic polymer, and at least one anti-acne agent, and
(b) at least one water-soluble substrate, and
removing the (b) at least one water-soluble substrate,
wherein the film (a) has a thickness ranging from 80 nm to 150 nm,
wherein the at least one anti-acne agent is present in the film (a) in an amount ranging from about 0.01% to about 30% by weight, relative to the total weight of the film (a), and
wherein the at least one anti-acne agent is incorporated inside the at least one biocompatible and/or biodegradable hydrophobic polymer layer of the film (a).

* * * * *

UNITED STATES PATENT AND TRADEMARK OFFICE
CERTIFICATE OF CORRECTION

PATENT NO. : 11,730,682 B2
APPLICATION NO. : 15/897650
DATED : August 22, 2023
INVENTOR(S) : Toshifumi Shiroya et al.

Page 1 of 1

It is certified that error appears in the above-identified patent and that said Letters Patent is hereby corrected as shown below:

In the Claims

Claim 1, Column 24, Line 25, change "anit-" to -- anti- --.

Signed and Sealed this
Fifth Day of August, 2025

Coke Morgan Stewart
*Acting Director of the United States Patent and Trademark Office*